United States Patent [19]

Yoneoka et al.

[11] Patent Number: 5,395,989

[45] Date of Patent: Mar. 7, 1995

[54] PROCESS FOR PRODUCING NEOPENTYL GLYCOL

[75] Inventors: Mikio Yoneoka; Kumiko Watabe; Gen Matsuda, all of Niigata, Japan

[73] Assignee: Mitsubishi Gas Chemical Company, Inc., Tokyo, Japan

[21] Appl. No.: 48,415

[22] Filed: Apr. 14, 1993

Related U.S. Application Data

[63] Continuation-in-part of Ser. No. 775,142, Oct. 9, 1991, abandoned.

[30] Foreign Application Priority Data

Nov. 6, 1990 [JP] Japan ................... 2-298912

[51] Int. Cl.$^6$ ............... C07C 29/14; C07C 31/20
[52] U.S. Cl. ....................... 568/862; 568/853
[58] Field of Search ................. 568/853, 862

[56] References Cited

U.S. PATENT DOCUMENTS

| | | | |
|---|---|---|---|
| 3,884,838 | 5/1975 | Fleming et al. | 252/470 |
| 3,920,760 | 11/1975 | Heinz | 568/853 |
| 4,149,009 | 4/1979 | Yoneoka et al. | 560/239 |
| 4,181,810 | 1/1980 | Immel et al. | 568/807 |
| 4,250,337 | 2/1981 | zur Hausen et al. | 368/853 |
| 4,851,592 | 7/1989 | Morris | 568/853 |
| 4,855,515 | 8/1989 | Morris et al. | 568/862 |
| 4,933,473 | 6/1990 | Ninomiya et al. | 568/862 |
| 5,004,845 | 4/1991 | Bradley et al. | 568/885 |
| 5,146,012 | 9/1992 | Salek | 568/853 |

FOREIGN PATENT DOCUMENTS

| | | |
|---|---|---|
| 44412 | 1/1982 | European Pat. Off. . |
| 0269888 | 6/1988 | European Pat. Off. . |
| 0434062A1 | 6/1991 | European Pat. Off. . |
| 899009 | 6/1962 | United Kingdom . |
| 1048530 | 11/1966 | United Kingdom . |
| 1219162 | 1/1971 | United Kingdom . |

*Primary Examiner*—Johann Richter
*Assistant Examiner*—Rebecca Cook
*Attorney, Agent, or Firm*—Frishauf, Holtz, Goodman & Woodward

[57] ABSTRACT

Disclosed is a process for producing neopentyl glycol which comprises hydrogenating hydroxypivaldehyde in the presence of a catalyst comprising copper, zinc and zirconium.

The catalyst has a high catalytic activity and a long service lifetime.

10 Claims, No Drawings

PROCESS FOR PRODUCING NEOPENTYL GLYCOL

REFERENCE TO RELATED APPLICATION

This application is a continuation-in-part application of application Ser. No. 07/775,142, filed Oct. 9, 1991, now abandoned the entire contents of which are hereby incorporated by reference.

BACKGROUND OF THE INVENTION

1. Field of the Invention

The present invention relates to a process for producing neopentyl glycol by hydrogenating hydroxypivaldehyde.

Neopentyl glycol is a very important intermediate for industrial use and has a wide variety of applications; for example, it is used in the production of various synthetic resins such as acrylic resins, polyester resins, polyurethane resins, alkyd resins and polycarbonate resins, and also used for a plasticizer, a synthetic lubricating oil, a fiber processing agent and a surfactant.

2. Description of the Related Arts

Neopentyl glycol has been usually produced by the following two processes.

In accordance with one of the processes, isobutyraldehyde and formaldehyde are subjected to an aldol condensation and then to a crossed Cannizzaro reaction in the presence of a strongly alkaline catalyst such as caustic soda, caustic potash, calcium hydroxide or the like to thereby produce the objective neopentyl glycol. This process, however, suffers a disadvantage that since sodium formate is by-produced in an equimolar amount to the objective product when caustic soda is used, the process fails to establish itself as a process for producing neopentyl glycol on a commercial scale insofar as sodium formate thus produced as the by-product can not be effectively utilized.

In accordance with another process, hydroxypivaldehyde as obtained by the reaction of isobutyraldehyde and formaldehyde is hydrogenated in the presence of a catalyst to thereby produce the objective neopentyl glycol, which process is not accompanied with sodium formate as the by-product.

The above-mentioned hydrogenation process is disclosed in Japanese Patent Publication Nos. 33169/1974 and 17568/1978, G.B. Pat. No. 1219162, U.S. Pat. No. 3,920,760, G.B. Pat. No. 1048530, European Patent Nos. 44412 and 44444, U.S. Pat. Nos. 4,855,515 and 4,933,473, etc, in which are disclosed Raney nickel, Ni-Cr, Cu-Zn, Cu-Al, Cu-Cr, Cu-Cr-Ba, Cu-Cr-Mn, Pt-Ru-W, etc. as catalysts for use in the hydrogenation reaction.

As mentioned above, in the process for producing neopentyl glycol by hydrogenating hydroxypivaldehyde, a variety of catalysts have been proposed. However, there still remain the problems in the above known catalysts that the catalytic activity is insufficient and thus the reaction must be carried out under high pressure conditions and that the catalytic activity can not be maintained at a high level for a long period of time since it is decreased under the influences of a slight amount of impurities contained in hydroxypivaldehyde as the starting material, and the like. Further, in the case of Raney nickel catalyst, in addition to the above defects in catalytic activity and persistency thereof, various problems still remain unsolved in that the catalyst can not be easily prepared and handled and that the process inevitably becomes complicated since the catalyst is used in a slurry form.

Moreover, with respect to a catalyst containing chromium, great care must be exercised in the production and handling of the catalyst for industrial use because of the toxicity of chromium. A catalyst containing platinum or ruthenium finds difficulty in the process for the preparation thereof and also in the regeneration thereof at the time of deterioration of the catalytic activity in spite of its using an expensive noble metal, thereby making itself unreasonably expensive. Water is generally used in the above-mentioned hydrogenation process as a solvent, but a low dissolution rate of hydroxypivaldehyde in water causes a troublesome and complicated problem with its dissolution in a industrial process plant.

SUMMARY OF THE INVENTION

As a result of intensive research and investigation made by the present inventors to solve the above-mentioned problems in the process for producing neopentyl glycol by hydrogenating hydroxypivaldehyde, it has been found that a catalyst comprising copper, zinc and zirconium completely different from the previously known catalysts has an extremely excellent performance, and that the hydrogenation reaction by the combined use of the above-mentioned novel catalyst with an organic solvent can produce neopentyl glycol advantageously on an industrial scale.

It is an object of the present invention to provide a process for producing neopentyl glycol by hydrogenating hydroxypivaldehyde with a high conversion and high selectivity.

It is another object of the present invention to provide a process for producing neopentyl glycol advantageously on an industrial scale by the use of a catalyst having a high strength and high catalytic activity for a long period of time.

The present invention relates to a process for producing neopentyl glycol which comprises hydrogenating hydroxypivaldehyde in the presence of a catalyst comprising copper, zinc and zirconium in the presence of at least one organic solvent selected from the group consisting of alcohols, ethers and hydrocarbons at a temperature of 60° to 250° C. and a pressure of 1 to 150 kg/cm$^2$.

DESCRIPTION OF THE PREFERRED EMBODIMENTS

In the present invention, a catalyst particularly comprising a copper oxide, zinc oxide and zirconium oxide has prominent performance with a high catalytic activity, persistency and strength.

In the present invention is used a solvent such as an alcohol exemplified by methanol, ethanol, proponol, butanol, hexanol, octanol and neopentyl alcohol; an ether exemplified by butyl ether, dioxane, etc.; a saturated hydrocarbon including n-heptane; mixture thereof, of which is desirable an alcohol, especially methanol. There are also usable as an organic solvent, neopentyl glycol that is the hydrogenation reaction product and a mixture of any of the aforesaid organic solvents and water. In the starting solution to be hydrogenated, there can coexist neopentyl glycol as the reaction product or hydrogenated reaction product containing a solvent. In practice, a solution of hydroxypivaldehyde in water and neopentyl glycol as the solvents can be used as a starting material.

By hydrogenating hydroxypivaldehyde which is obtained by the condensation of isobutyraldehyde and formaldehyde, through the use of a catalyst comprising copper, zinc and zirconium in the presence of the above solvents, neopentyl glycol is consistently industrially obtained at a high yield.

In the following, the present invention will be described in more detail.

Firstly, hydroxypivaldehyde to be used in the present invention can be obtained with ease by subjecting isobutyraldehyde and formaldehyde to aldol condensation reaction in the presence of an alkaline catalyst. For example, hydroxypivaldehyde to be used in the present invention can be obtained by the above condensation reaction in a molar feed ratio of isobutyraldehyde to formaldehyde of 0.8–1.3, preferably 1.1–1.2, at 15° to 95° C. in the presence of a tertiary amine catalyst such as trimethylamine, triethylamine, etc. or at 15° to 40° C. in the presence of a strongly alkaline catalyst such as caustic soda, etc.

As hydroxypivaldehyde for the starting material according to the process of the present invention, there can be used (1) the above-mentioned aldol condensation reaction product from which unreacted isobutyraldehyde and formaldehyde are removed; (2) the reaction product from which the aforesaid unreacted aldehydes and tertiary amine catalyst are removed; (3) the reaction product as it is; or (4) the reaction product from which the unreacted isobutyraldehyde and formaldehyde are removed followed by crystallization of the dimer of hydroxypivaldehyde in water. The dimer can be used in the process of the present invention without any troubles since it takes part as a hydroxypivaldehyde monomer in the hydrogenation reaction. In addition, (5) extraction solution of hydroxypivaldehyde from aldol condensation liquid obtained by using an alcohol having at least 4 carbon atoms can also be employed as a starting material.

In the case of carrying out the process of the present invention, a starting solution of the hydroxypivaldehyde in a proper amount of the above-mentioned organic solvent or water in addition thereto is prepared and subsequently subjected to hydrogenation reaction in the presence of a catalyst comprising copper, zinc and zirconium. In the above starting solution are usually contained impurities such as unreacted isobutyraldehyde, formaldehyde, tertiary amine, amine compounds derived therefrom, formate, etc. The maximum allowable content of the impurities is 0.5% by weight.

In the case where the dimer of hydroxypivaldehyde obtained through crystallization from the condensation reaction liquid of isobutyraldehyde and formaldehyde is used as the starting material, the dimer is preferably dissolved in a solvent to proceed with reaction. As the solvent, there is particularly desirably used an alcohol such as methanol and a mixture thereof with water. In the case of the mixed solvent of water and methanol, they can be used in an optional proportion.

The catalyst according to the present invention is not specifically limited with regard to the process for preparation thereof so long as it comprises copper, zinc and zirconium, but can be prepared by the previously known process. For example, a copper oxide, zinc oxide and zirconium oxide are mixed together in the form of powder or paste incorporated with water and formed into a desirable catalyst. Alternatively, the precipitates obtained from soluble salts of copper and zinc, respectively and a precipitant are made into a copper oxide and zinc oxide, respectively, which are then mixed with a zirconium oxide and formed into a desirable catalyst.

In the light of the stability and reproducibility of the performance of the catalyst obtained, it is preferable to produce a catalyst precursor by the following Process (1) to (3), and to calcine the precursor into a catalyst comprising a copper oxide and zirconium oxide.

Process (1) wherein a catalyst precursor is prepared by combining a precipitate obtained by mixing the aqueous solution of a copper salt with the aqueous solution of a precipitant and a precipitate obtained by mixing the aqueous solution of a zinc salt with the aqueous solution of a precipitant, and adding a zirconium precipitate which was already prepared separately to the combined precipitate.

Process (2) wherein a catalyst precursor is prepared by mixing a zirconium precipitate which was already prepared separately to a coprecipitate obtained by mixing the mixed aqueous solution of a copper salt and a zinc salt with a precipitant.

Process (3) wherein a catalyst precursor is prepared by coprecipitating the mixed aqueous solution of a copper salt, a zinc salt and a zirconium salt.

In the above-described processes for the preparation of the catalyst precursor, copper and zinc are used in the form of water-soluble salts, which are exemplified by nitrate, hydrochloride, sulfate, acetate, etc. Among them, nitrate and acetate are preferably used. In the case where zinc oxide powder is used as a starting material, $CO_2$ injection method can be used. Zirconium is used also in the form of water-soluble salt, which is exemplified by zirconium alkoxide, zirconyl nitrate, zirconium acetate, etc.

Examples of precipitants to be employed for precipitate formation include caustic alkali such as sodium hydroxide and lithium hydroxide, carbonate alkali such as sodium carbonate, potassium carbonate, lithium carbonate and ammonium carbonate, bicarbonate alkali such as sodium bicarbonate, potassium bicarbonate and ammonium bicarbonate, and aqueous ammonia. The precipitate formation reaction can be carried out at 90° C. or lower, even at room temperature.

The atomic ratio of zinc to copper is not limited, but is usually 0.05 to 2:1, preferably 0.07 to 1.5:1 in the catalyst comprising copper, zinc and zirconium according to the present invention. An atomic ratio of zinc to copper outside the above-mentioned scope lowers the catalytic activity, is likely to form an acetal compound of neopentyl glycol with hydroxypivalhyde as a by-product and a by-product due to hydrogenation cracking, and shortens the service life of the catalyst. Zirconium in the catalyst is preferably present in the form of an oxide and in the atomic ratio of 0.05 to 2, preferably 0.07 to 1.7 based on copper.

The catalyst precursor in the form of a mixture as obtained by the aforestated preparation process is dried at a temperature higher than room temperature, preferably at 80° to 130° C., calcinated at 200° to 800° C. and thereafter formed in accordance with a specific embodiment to serve as the catalyst of the present invention.

In the case of the catalyst formation, a filler such as diatomaceous earth, silica, graphite or the like can be mixed in the catalyst precursor in the form of mixture to the extent that the filler does not impair the reaction which proceeds in the present invention. A filler may be added during the preparation of the precursor such as the precipitates of copper and zinc or those of copper, zinc and zirconium or prior to the formation of a catalyst.

The catalyst thus obtained is reduced in advance with a reductive gas such as hydrogen to activate itself and thereafter brought into use for the reaction. It is also possible to activate the catalyst in a reactor by introducing methanol vapor thereinto.

In the following, the reaction which proceeds in the present invention will be explained in more detail.

The hydroxypivaldehyde in a starting solution to be employed for hydrogenation reaction should have a concentration of 5 to 80% by weight, preferably 15 to 60% by weight. A concentration lower than the lower limit of the above range causes difficulty in the separation of neopentyl glycol from a solvent and further, increases the energy burden required for separating the solvent by evaporation. On the other hand, a concentration higher than the upper limit of the above range causes Tischenko reaction to take place between the hydroxypivaldehydes themselves resulting in the by-product of neopentyl glycol ester of hydroxypivaldehyde, which is not advantageous for industrial use.

For hydrogenation reaction of hydroxypivaldehyde according to the process of the present invention, the catalyst comprising copper, zinc and zirconium is dispersed or suspended in the solution of hydropivaldehyde as the starting material in the above-mentioned solvent in the coexistence of hydrogen, or the starting material solution is fed to a column packed with the above catalyst in the coexistence of hydrogen.

The hydrogenation reaction can be effected by either continuous process or batch wise process.

The reaction temperature is 60° to 250° C., preferably 80° to 200° C.

The reaction pressure is 1 to 150 kg/cm$^2$, preferably 5 to 80 kg/cm$^2$, which is maintained by introducing hydrogen.

After the completion of the reaction, the objective neopentyl glycol is recovered by separation from the reaction product by means of distillation or solvent extraction.

According to the process for producing neopentyl glycol by hydrogenating hydroxypivaldehyde, a sufficient catalytic activity and selectivity are exhibited, and a stable and long-term service life of the catalyst is realized, thereby rendering the present invention highly significant for an industrial use.

In what follows, the present invention will be described in more detail with reference to the following examples, which however, are not intended to limit thereto the process of the present invention.

In the Examples and Comparative Examples, hydroxypivaldehyde, neopentyl glycol, isobutyraldehyde, triethylamine and hydroxypivalic acid neopentyl glycol ester are abbreviated to HPA, NPG, IBA, TEA, and HPNE, respectively. The catalyst composition is expressed by the atomic ratio for copper, zinc and zirconium.

The aldol condensation solution used for catalytic activity evaluation test was prepared by reacting IBA with 40% formalin in the presence of TEA as a catalyst, and adding water and methanol thereto so as to attain a concentration of HPA of about 25% by weight. The composition by weight of the solution thus obtained was 25.02% of HPA, 0.03% of IBA, 0.42% of TEA, 49.20% of methanol, 24.82% of water, 0.08% of HPNE, 0.22% of NPG and 0.2% of others.

EXAMPLE 1

550 g of aqueous zirconyl nitrate solution (25% as ZrO$_2$) was dissolved in 2.5 L(liter) of deionized water and maintained at 40° C. The above solution thus obtained was added to the solution of 197.5 g of ammonium bicarbonate in 5 L of deionized water at 40° C. with stirring, maintained at 40° C. for 30 minutes and then, the mixture was filtered and washed to afford about 830 g of cake as the source of zirconium oxide.

Then, 570 g of copper nitrate (trihydrate) was dissolved in 4.4 L of deionized water and maintained at 40° C. After 283 g of sodium carbonate anhydride was dissolved in 3.5 L of deionized water and kept at 40° C., the mixture was added with the above aqueous solution of copper nitrate with stirring to produce copper slurry. A solution of 347 g of zinc nitrate (hexahydrate) in 1 L of deionized water and a solution of 145 g of sodium carbonate anhydride in 1 L of deionized water each at 40° C. were simultaneously added to the copper slurry. The mixture was held at 40° C. for 40 minutes, heated to 70° C., held at 70° C. for 30 minutes and thereafter subjected to filtration and washing to give about 830 g of cake.

Then, 500 g of the cake containing copper and zinc and 390 g of the cake as the source of zirconium oxide were placed in a milling apparatus and kneaded to produce a paste, which was dried at 80° C., calcinated at 380° C. for 2 hours, pulverized to 32 mesh, added with graphite by 3% by weight with mixing and tableted. The tableted catalyst was pulverized to 20–32 mesh, reduced in a mixed gas stream of N$_2$–H$_2$ at 170° C. for activation.

A stainless steel autoclave having an internal capacity of 100 ml was fed with 15 g of aldol solution and 1 g of activated catalyst, and closed up with a lid. Then, hydrogen gas was introduced into the autoclave to replace the air space and attain a pressure of 20 kg/cm$^2$.

The autoclave was placed on a shaking stand. While shaking the autoclave, the reaction was carried out by raising the temperature of the contents therein to 110° C. After the completion of the reaction, the autoclave was cooled with ice-cold water and depressurized. The liquid reaction product was analyzed by gas chromatography. The results are shown in Table 1 together with the reaction conditions.

EXAMPLE 2

400 g of ammonium bicarbonate was dissolved in 20 L of deionized water and held at 40° C. Separately, 317 g of copper nitrate (trihydrate) and 295 g of zinc nitrate (hexahydrate) were dissolved in 5 L of deionized water and added with the above bicarbonate solution with stirring. The resultant mixture was heated to 80° C. for 30 minutes, kept at 80° C. for 30 minutes and then, cooled to 40° C.

Individually, 328 g of ammonium bicarbonate was dissolved in 10 L of deionized water and held at 40° C. 378 g of zirconyl nitrate (dihydrate) was dissolved in 5 L of deionized water and added with the above ammonium bicarbonate solution with stirring to form precipitate.

The zirconium-containing slurry and the slurry containing copper and zinc were mixed with stirring, held for 30 minutes and then subjected to filtration and washing to give a cake.

The steps including and after the cake drying step were carried out in the same manner as in Example 1 to prepare the catalyst. The procedure in Example 1 was repeated in the evaluation test for catalyst activity except that a 15 g of solution of HPA with 25% concentration in methanol was used in place of aldol solution and that different reaction conditions from Example 1 were applied. The results are shown in Table 1 together with the reaction conditions.

EXAMPLE 3

1.42 kg of copper nitrate (trihydrate) and 350 g of zinc nitrate (hexahydrate) were dissolved in 14 L of deionized water to prepare a copper-zinc solution and kept at 40° C. Separately, 1.23 kg of ammonium bicarbonate was dissolved in 30 L of deionized water and added with the above copper-zinc solution while stirring. The temperature of the resultant mixture was raised to 70° C. for 30 minutes, held thereat for 30 minutes and then lowered to 40° C. by cooling. The copper-zinc slurry was added with a solution of 3.38 kg of aqueous zirconyl nitrate solution (25% as $ZrO_2$) in 13 L of deionized water at 40° C. and a solution of 1.22 kg of ammonium bicarbonate in 30 L of deionized water at 40° C. each while stirring and mixed together. The resultant mixture was kept at 40° C. for 30 minutes and subsequently subjected to filtration and washing to produce a cake. The steps after the cake formation as mentioned above were carried out in the same manner as in Example 1 to prepare the catalyst. The procedure in Example 1 was repeated in the evaluation test for the activity of the catalyst thus obtained except that a solution of 3.8 g of HPA powder in 12 g of mixed solvent of water and NPG in a ratio of 1:2 was used in place of aldol solution and that different reaction conditions from Example 1 were applied. The results are shown in Table 1 together with the reaction conditions.

EXAMPLE 4

12.45 kg of copper nitrate (trihydrate) was dissolved in 77.5 L of deionized water and held at 40° C. Then, 9.20 kg of ammonium bicarbonate was dissolved in 90 L of deionized water. The mixed solution was held at 40° C. and added with the above copper nitrate solution while stirring to prepare copper slurry. Separately, 0.84 kg of zinc oxide was placed in 33.3 L of deionized water with stirring for 30 minutes to prepare zinc oxide slurry, which was added to the above copper slurry. The resultant copper-zinc slurry was injected with carbon dioxide gas at a rate of 4.8 L/min, maintained at 40° C., heated to 70° C. after 40 minutes, held at 70° C. for 30 minutes, then cooled to 40° C., added with a solution of 16.82 kg of aqueous zirconyl nitrate solution (25% as $ZrO_2$) in 41.7 L of deionized water at 40° C. and a solution of 6.08 kg of ammonium bicarbonate in 75 L of deionized water at 40° C. each while stirring, and held at 40° C. for 30 minutes. The mixture was filtered and washed to produce a cake, which was dried at 80° C., calcinated at 380° C. for 2 hours, crushed, pulverized to 8-12 mesh and reduced in a mixed gas stream of $N_2$-$H_2$ at 170° C. for the activation of the catalyst. The procedure of Example 1 was repeated in the evaluation test for the catalyst activity except that a solution of 3.8 g of HPA powder in 12 g of mixed solvent of water and methanol in a ratio of 1:2 was used and that different reaction conditions from Example 1 were applied. The results are shown in Table 1 along with the reaction conditions.

TABLE 1

| Example | 1 | 2 | 3 | 4 |
|---|---|---|---|---|
| Catalyst Mesh | 20 to 32 | 8 to 12 | 8 to 12 | 8 to 12 |
| (g) | 1.0 | 2.0 | 1.0 | 1.0 |
| Starting material HPA powder (g) | — | — | 3.8 | 3.8 |
| 25% HPA solution (g) | — | 15 | — | — |
| Solvent | water-methanol | methanol | water-NPG | water-methanol |
| Aldol solution (g) | 15 | — | — | — |
| Hydrogen charge pressure (kg/cm$^2$) | 20 | 35 | 60 | 35 |
| Reaction temperature (°C.) | 110 | 110 | 120 | 100 |
| Reaction time (min.) | 55 | 60 | 35 | 60 |
| RPA conversion (mol %) | 99.7 | 99.9 | 98.8 | 100 |
| NPG selectivity (mol %) | 98.1 | 98.9 | 97.6 | 99.0 |

EXAMPLES 5 to 8

120.8 g of copper nitrate (trihydrate), 29.75 g of zinc nitrate (hexahydrate) and 89.8 g of zirconyl nitrate (dihydrate) were dissolved in 1.9 L of deionized water. The mixed solution was held at 75° C. and added to a solution of 116 g of sodium carbonate anhydride in 1.2 L of deionized water with stirring to form precipitate. The resultant slurry was maintained at 75° C. for 90 minutes, then cooled and filtered. The cake thus obtained was washed with deionized water, dried at 115° C. for 13 hours and calcinated in the air at 350° C. for 2 hours. The calcinated product was added with graphite and tableted. The catalyst had an atomic ratio of copper, zinc and zirconium of 10:2:6.7. In the same manner as above, additional three catalysts having atomic ratios of copper, zinc and zirconium of 10:0.5:10, 10:15:0.5 and 10:2:3, respectively were prepared and subjected to activity evaluation test by batchwise system.

The reaction conditions for activity evaluation test were as follows: catalyst: 8 to 12 mesh, 1 g starting material: aldol condensation reaction liquid (HPA 25% by weight) 15 g hydrogen charge pressure: 35 kg/cm$^2$ reaction temperature: 100° C. reaction time: 60 minutes The reaction performance by each catalyst composition is indicated in Table 2.

TABLE 2

| Example | 5 | 6 | 7 | 8 |
|---|---|---|---|---|
| Cu:Zn:Zr ratio | 10:2:6.7 | 10:0.5:10 | 10:16:0.5 | 10:2:3 |
| HPA conversion (mol %) | 97.0 | 83.9 | 83.4 | 96.2 |
| HPG selectivity (mol %) | 99.0 | 98.8 | 98.9 | 99.0 |

EXAMPLE 9

The catalyst as described in Example 4 was crushed to 3 to 4 mm and a portion thereof having a volume of 150 ml was packed in a stainless steel single-tube reactor. HPA solution as the starting material and hydrogen were continuously introduced into the reactor to effect continuous reaction for 130 days. The composition of the starting material solution is the same as that in Example 1. The reaction conditions and the trend of reaction performance are listed in Table 3. It can be seen from Table 3 that the catalyst according to the present invention maintains a high catalytic activity for a long period of time.

TABLE 3

| Number of operating days (days) | 1 | 50 | 80 | 130 |
|---|---|---|---|---|
| LSV* ($hr^{-1}$) | 1.9 | 2.0 | 2.0 | 2.0 |
| Pressure ($kg/cm^2$) | 30 | 30 | 30 | 30 |
| Temperature (°C.) | 125 | 125 | 125 | 125 |
| HPA conversion (mol %) | 100 | 100 | 100 | 100 |
| NPG selectivity (mol %) | 98.9 | 99.0 | 99.0 | 99.0 |

*LSV: liquid hourly space velocity

COMPARATIVE EXAMPLES 1 to 4

The procedures in Examples 5 to 8 were repeated except that catalysts having atomic ratios of copper to zinc of 10:0.5, 10:2 and 10:15, respectively, and a marketed catalyst comprising copper, chromium and manganese (N-201, available from NIKKI CHEMICAL CO., LTD.) were used to carry out hydrogenation reaction.

The reaction performance for each of the catalyst is shown in Table 4.

TABLE 4

| Comparative Example | 1 | 2 | 3 | 4 |
|---|---|---|---|---|
| Catalyst | Cu—Zn 10:0.5 | Cu—Zn 10:2 | Cu—Zn 10:15 | N-201 |
| HPA conversion (mol %) | 40.0 | 61.7 | 55.4 | 60.3 |
| NPG selectivity (mol %) | 92.2 | 89.7 | 88.6 | 79.6 |

COMPARATIVE EXAMPLE 5

120.6 g of copper nitrate (trihydrate) and 9.35 g of zirconium oxynitrate (dihydrate) were dissolved in 1.7 L of deionized water and kept at 73° C. Separately, 68.04 g of sodium carbonate anhydride was dissolved in 1 L of deionized water to form a solution and maintained at 75° C. The solution was added to the mixed solution of copper nitrate and zirconium oxynitrate with stirring to form precipitate. The slurry thus obtained was held at 75° C. for 90 minutes, then cooled and filtered. The resultant cake was washed, dried at 115° C. for 12 hours, calcinated in the air at 350° C. for 2 hours, added with graphite and formed into tablets. The tablets thus obtained were pulverized to 8–12 mesh and reduced in a mixed gas stream of $N_2$-$H_2$ at 170° C. In the same manner as in Examples 5–8, the catalyst was subjected to the activity evaluation test. The results are shown in Table 5 along with the reaction conditions.

COMPARATIVE EXAMPLE 6

1.41 kg of copper nitrate (trihydrate) was dissolved in 12 L of deionized water and held at 40° C. The resultant solution was added with a solution of 1.02 kg of ammonium bicarbonate in 29 L of deionized water at 40° C. while stirring. Thereafter, the temperature was raised to 70° C. for 30 minutes, maintained thereat for 30 minutes and lowered to 40° C. by cooling.

The copper slurry thus formed was added with a solution of 869 g of zirconyl nitrate solution (25% as $ZrO_2$) in 10 L of deionized water at 40° C. and a solution of 310.9 g of ammonium bicarbonate in 12 L of deionized water at 40° C. each with stirring and held at 40° C. for 30 minutes. The resultant slurry was filtered, and the cake formed was washed and subjected to calcination, forming and reduction in the same manner as in Comparative Example 5. The activity evaluation test for the catalyst thus obtained was performed in the same manner as in Examples 5 to 8. The results are shown in Table 5 along with the reaction conditions.

COMPARATIVE EXAMPLE 7

400 g of ammonium bicarbonate was dissolved in 18 L of deionized water and held at 40° C. The resultant solution was added with a solution of 317 g of copper nitrate (trihydrate) in 4 L of deionized water at 40° C. while stirring. Thereafter, the temperature was raised to 80° C. for 30 minutes, kept thereat for 30 minutes and lowered to 40° C. by cooling. Separately, a solution at 40° C. of 596 g of zirconyl nitrate (dihydrate) in 6 L of deionized water was added with stirring to a solution at 40° C. of 393.2 g of ammonium bicarbonate in 8 L of deionized water to form precipitate. The slurry thus formed was mixed with the copper slurry while stirring, and the resultant slurry mixture ws held for 30 minutes and then filtered. The cake formed was washed and subjected to calcination, forming and reduction in the same manner as in Comparative Example 5. The activity evaluation test for the catalyst thus obtained was carried out in the same manner as in Examples 5 to 8. The results are shown in Table 5 along with the reaction conditions.

TABLE 5

| Comparative Example | 5 | 6 | 7 |
|---|---|---|---|
| Catalyst | Cu—Zr 10:0.7 | Cu—Zr 10:3 | Cu—Zr 10:17 |
| HPA conversion (mol %) | 66.7 | 51.3 | 48.7 |
| NPG selectivity (mol %) | 88.0 | 76.9 | 75.4 |

What is claimed is:

1. A process for producing neopentyl glycol which comprises hydrogenating hydroxypivaldehyde in the presence of a catalyst comprising copper, zinc and zirconium and in the presence of a solvent selected from the group consisting of (i) at least one alcohol selected from the group consisting of methanol, ethanol, propanol, butanol, hexanol, octanol and neopentyl glycol and (ii) water and at least one alcohol selected from the group consisting of methanol, ethanol, propanol, butanol, hexanol, octanol and neopentyl glycol, at a temperature of 60° to 250° C. and a pressure of 1 to 150 $kg/cm^2$ maintained by introducing hydrogen.

2. The process as claimed in claim 1, wherein the hydroxypivaldehyde comprises an aldol condensation reaction solution which is obtained by reacting isobutyraldehyde with formaldehyde in the presence of a base catalyst.

3. The process as claimed in claim 1, wherein the hydrogenation is effected at a temperature of 80° to 200° C. and a pressure of 5 to 80 $kg/cm^2$.

4. The process as claimed in claim 1, wherein the catalyst has an atomic ratio of zinc to copper of 0.05:1 to 2:1 and an atomic ratio of zirconium to copper of 0.05:1 to 2:1.

5. The process as claimed in claim 1, wherein the catalyst has an atomic ratio of zinc to copper of 0.07:1 to 1.5:1 and an atomic ratio of zirconium to copper of 0.07:1 to 1.5:1.

6. The process as claimed in claim 1, wherein the catalyst is prepared by (a) combining (i) a first precipitate obtained by mixing an aqueous solution of a copper salt with an aqueous solution of first precipitant selected from the group consisting of caustic alkali, carbonate alkali, bicarbonate alkali and ammonia; and (ii) a second precipitate obtained by mixing an aqueous solution of a zinc salt with an aqueous solution of second precipitant selected from the group consisting of caustic alkali, carbonate alkali, bicarbonate alkali and ammonia, (b) mixing therewith a zirconium precipitate which was prepared separately, to produce a catalyst precursor, and (c) calcining the precursor.

7. The process as claimed in claim 1, wherein the catalyst is prepared by mixing a zirconium precipitate which was prepared separately with a coprecipitate obtained by mixing a mixed aqueous solution of a copper salt and a zinc salt with a precipitant selected from the group consisting of caustic alkali, carbonate alkali, bicarbonate alkali and ammonia to produce a catalyst precursor, and calcining the precursor.

8. The process as claimed in claim 1, wherein the catalyst is prepared by coprecipitating a mixed aqueous solution of water-soluble salts of copper, zinc and zirconium in the presence of a precipitant selected from the group consisting of caustic alkali, carbonate alkali, bicarbonate alkali and aqueous ammonia to produce a catalyst precursor, and calcining the catalyst precursor.

9. The process as claimed in claim 1, wherein the hydroxypivaldehyde is in a solution in a concentration of 5 to 80% by weight.

10. The process as claimed in claim 9, wherein the hydroxypivaldehyde is in a concentration of 15 to 60% by weight.

* * * * *